US009744364B2

(12) United States Patent
Gordon et al.

(10) Patent No.: US 9,744,364 B2
(45) Date of Patent: Aug. 29, 2017

(54) METHOD AND APPARATUS FOR AUTOMATIC CONFIGURATION OF IMPLANTABLE MEDICAL DEVICES

(71) Applicant: Medtronic, Inc., Minneapolis, MN (US)

(72) Inventors: Charles R Gordon, Phoenix, AZ (US); Paul G Krause, Shoreview, MN (US); Grant Alan Neitzell, Fridley, MN (US); Shantanu Sarkar, Roseville, MN (US); Ryan Wyszynski, Oak Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 228 days.

(21) Appl. No.: 14/248,939

(22) Filed: Apr. 9, 2014

(65) Prior Publication Data

US 2015/0088216 A1    Mar. 26, 2015

Related U.S. Application Data

(60) Provisional application No. 61/882,387, filed on Sep. 25, 2013.

(51) Int. Cl.

| *A61N 1/00* | (2006.01) |
| *A61N 1/37* | (2006.01) |
| *A61N 1/362* | (2006.01) |
| *A61B 5/00* | (2006.01) |
| *G06F 19/00* | (2011.01) |

(52) U.S. Cl.
CPC .......... *A61N 1/3704* (2013.01); *A61B 5/0006* (2013.01); *A61B 5/0031* (2013.01); *A61N 1/3624* (2013.01); *G06F 19/3418* (2013.01); *G06F 19/3481* (2013.01)

(58) Field of Classification Search
CPC ..................................................... A61N 1/3704
USPC ........................................................ 607/9, 14
See application file for complete search history.

(56) References Cited

U.S. PATENT DOCUMENTS

| 4,550,370 A | 10/1985 | Baker |
| 5,331,966 A * | 7/1994 | Bennett .............. A61N 1/36185 |
| | | 128/903 |

(Continued)

OTHER PUBLICATIONS

C00006099.WOU3 (PCT/US2014/049865) PCT Notification of Transmittal of the International Search Report and the Written Opinion of the International Searching Authority, Mailed Nov. 7, 2014, 12 pages.

*Primary Examiner* — Christopher D Koharski
*Assistant Examiner* — Nadia A Mahmood (57) ABSTRACT

A system including a programmable implantable monitoring device and a programmer for programming the device and a method of use thereof. The programmer may be configured to transmit programming commands responsive to entry of a reason for monitoring to the implantable device including a prioritization of an arrhythmia storage criterion. The implantable may be configured to thereafter store and/or transmit records of the arrhythmia according to the prioritization. The programmer may be configured to transmit the patient's age to the implantable device and the implantable may be configured to thereafter apply arrhythmia detection criteria based upon the patient's age.

19 Claims, 4 Drawing Sheets

(56) References Cited

U.S. PATENT DOCUMENTS

| | | | |
|---|---|---|---|
| 5,607,460 A * | 3/1997 | Kroll | A61N 1/37247 607/30 |
| 5,785,660 A | 7/1998 | Van Lake et al. | |
| 5,944,745 A | 8/1999 | Rueter | |
| 5,987,352 A | 11/1999 | Klein et al. | |
| 6,230,059 B1 | 5/2001 | Duffin | |
| 6,236,882 B1 | 5/2001 | Lee et al. | |
| 6,381,493 B1 | 4/2002 | Stadler et al. | |
| 6,412,490 B1 | 7/2002 | Lee | |
| 6,496,715 B1 | 12/2002 | Lee et al. | |
| 6,589,187 B1 * | 7/2003 | Dirnberger | A61B 5/0432 365/230.01 |
| 7,035,684 B2 | 4/2006 | Lee | |
| 7,130,678 B2 | 10/2006 | Ritscher et al. | |
| 7,528,094 B2 | 5/2009 | Blaha et al. | |
| 2006/0020292 A1 | 1/2006 | Goetz et al. | |
| 2008/0051843 A1 * | 2/2008 | Li | A61N 1/3622 607/9 |
| 2009/0036917 A1 | 2/2009 | Anderson | |
| 2010/0094252 A1 | 4/2010 | Wengreen et al. | |
| 2010/0283705 A1 | 11/2010 | Achour et al. | |
| 2010/0297594 A1 | 11/2010 | Sullivan et al. | |
| 2011/0098637 A1 | 4/2011 | Hill | |
| 2012/0046704 A1 | 2/2012 | Gilkerson et al. | |

* cited by examiner

METHOD AND APPARATUS FOR AUTOMATIC CONFIGURATION OF IMPLANTABLE MEDICAL DEVICES

CROSS-REFERENCE TO RELATED APPLICATIONS

This application claims the benefit of U.S. Provisional Application No. 61/882,387, filed on Sep. 25, 2013. The disclosure of the above application is incorporated herein by reference in its entirety.

FIELD OF THE INVENTION

This invention relates to an implantable monitoring device for sensing physiologic events with minimally invasive intrusion into an animal or patient body, and is particularly well suited for long term monitoring of body events like ElectroCardioGrams (ECG's) and in monitoring other body physiologic events related to heart function. The invention may be included in a simple monitor or in an implantable device that also performs other functions such as cardiac pacing, defibrillation, nerve stimulation, drug delivery and the like.

BACKGROUND OF THE INVENTION

Over the last 40 years, a great many IMDs have been clinically implanted in patients to treat cardiac arrhythmias and other disorders including implantable cardioverter/defibrillators (ICDs) and pacemakers having single or dual chamber pacing capabilities, cardiomyostimulators, ischemia treatment devices, and drug delivery devices. Recently developed implantable pacemakers and ICDs have been provided with sophisticated arrhythmia detection and discrimination systems based on heart rate, the morphology and other characteristics of the atrial and ventricular EGM and other characteristics of the EGM. Most of these IMDs employ electrical leads bearing bipolar electrode pairs located adjacent to or in a heart chamber for sensing a near field EGM or having one of the electrodes located on the IMD housing for sensing a far field, unipolar EGM. In either case, the near field or far field EGM signals across the electrode pairs are filtered and amplified in sense amplifiers coupled thereto and then processed for recording the sampled EGM or for deriving sense event signals from the EGM.

In current IMDs providing a therapy for treating a cardiac arrhythmia, the sense event signals and certain aspects of the sampled EGM waveform are utilized to automatically detect a cardiac arrhythmia and to control the delivery of an appropriate therapy in accordance with detection and therapy delivery operating algorithms. In such cardiac IMDs providing pacing or cardioversion/defibrillation therapies, both analog and digital signal processing of the EGM is continuously carried out to sense the P-wave and/or R-wave events and to determine when a cardiac arrhythmia episode occurs. For example, a digital signal processing algorithm is employed to distinguish various atrial and ventricular tachyarrhythmias from one another. When a tachyarrhythmia episode is detected, at least selected EGM signal segments and sense event histogram data or the like are stored on a FIFO basis in internal RAM for telemetry out to an external programmer at a later time. Many of these IMDs are also capable of being operated to sample the EGM and transmit real time EGM data of indefinite length via uplink telemetry transmissions to the external programmer when a real time telemetry session is initiated by the medical care provider using the programmer.

Implantable cardiac monitors have also been developed and clinically implanted that employ the capability of recording cardiac EGM data for subsequent interrogation and uplink telemetry transmission to an external programmer for analysis by a physician. The recorded data is periodically telemetered out to a programmer operated by the medical care provider in an uplink telemetry transmission during a telemetry session initiated by a downlink telemetry transmission and receipt of an interrogation command.

The MEDTRONIC® Reveal™ insertable loop recorder is a form of implantable monitor that is intended to be implanted subcutaneously and has a pair of sense electrodes spaced apart on the device housing that are used to pick up the cardiac far field EGM which in this case is also characterized as a "subcutaneous ECG". The Reveal™ insertable loop recorder samples and records one or more segment (depending on the programmed operating mode) of such far field EGM or subcutaneous ECG signals when the patient feels the effects of an arrhythmic episode and activates the recording function by applying a magnet over the site of implantation. For example, the storage of a programmable length segment of the EGM can be initiated when the patient feels faint due to a bradycardia or tachycardia or feels the palpitations that accompany certain tachycardias. The memory capacity is limited, and so the segments of such EGM episode data that are stored in memory can be written over with new EGM episode data when the patient triggers storage and the memory is full. The most recently stored segment or segments of episode data is transmitted via an uplink telemetry transmission to an external programmer when a memory interrogation telemetry session is initiated by the physician or medical care provider using the programmer. Aspects of the Reveal™ insertable loop recorder are disclosed in commonly assigned PCT publication WO98/02209, incorporated by reference herein in its entirety.

More complex implantable monitors and pacemaker IPGs of this type but having more electrodes arranged in a planar array on the device housing are disclosed in commonly assigned U.S. Pat. No. 5,331,966, incorporated herein by reference in its entirety. Three electrodes are employed to provide a pair of orthogonal sensed EGM or "subcutaneous ECG" signals at the subcutaneous implantation site. A lead can be employed in a disclosed pacemaker embodiment to locate a bipolar electrode pair in a heart chamber to provide an additional near field EGM sense signal from which the P-wave or R-wave can be sensed (depending on the location of the bipolar electrode pair) and through which pacing pulses can be applied to the atrium or ventricle. Recording of the near field and far field EGM episode data can be invoked automatically by detection of a bradycardia or satisfaction of tachyarrhythmia detection criteria or can be manually commenced by the patient using an external limited function programmer or can be commenced by the physician using a full function programmer.

In all of these IMDs having a cardiac monitoring function, the cardiac EGM is continually sensed and sampled in such monitors and recording of EGM episode data is triggered in a variety of ways. The relatively inexpensive and simple to implant Reveal™ insertable loop recorder has been favorably compared to the "black box" of an aircraft by physicians that have prescribed its implantation and use in a number of patients. Recordings of EGM episode data triggered by the patient using the relatively simple Reveal™ insertable loop recorder have proven to be of great value in diagnosing the causes of symptoms felt by the patients and in prescribing the implantation and programming of more complex therapy delivery IMDs, e.g., multi-programmable physiologic DDDR pacemakers and single and dual chamber ICDs.

A variety of other programmable implantable medical devices such as hemodynamic monitors and other physiological monitors are available. These include both implantable pacemakers and defibrillators as well as subcutaneous monitors, for example as disclosed in U.S. Pat. Nos. 5,331,966, 5,987,352, 6,230,059, 6,236,882, 6,381,493 and 7,035,684, all incorporated by reference herein in their entireties.

Programming commands or data are typically transmitted between an implanted RF telemetry antenna and associated circuitry and an external RF telemetry antenna associated with the external programmer. The transmitted telemetry to the implanted device typically allows the physician to program the operation of the device. In the context of implantable ECG monitors, for example, as discussed in the above cited references, extensive programming options may be available directed to the types of arrhythmias to be detected, the criteria for detecting the arrhythmias and the storage of Data related to the detected arrhythmias. One commercially available subcutaneous monitor of this type is the Reveal AF™ device, available from Medtronic, Inc.

Because memory space is limited in such devices, Prioritization of stored data is desirable so the physician can be sure that the information of highest priority is preferentially stored. Exemplary data prioritization schemes are disclosed in U.S. Pat. Nos. 6,230,059, 6,236,882, 5,944,745, 7,130,678 and 6,589,187, all incorporated herein by reference. Normally, the physician has the option of setting the priorities for data storage by means of the external programmer.

Such devices also typically have arrhythmia detection capabilities which the physician may also set to conform to the patient's condition, by means of activation or deactivation of arrhythmia detection mechanisms and by adjusting particular parameters associated with arrhythmia detection, such as heart rates. Exemplary detection mechanisms for implantable devices are disclosed in U.S. Pat. Nos. 6,236,882, 6,381,493, all incorporated herein by reference.

Because programming of implantable devices can be complex and time consuming, mechanisms have been proposed for simplifying this process. Such mechanisms are sometimes known as "Programming Wizards". Such mechanisms are disclosed in US Patent Publication Nos. 20110098637 and 20060020292, incorporated herein by reference in their entireties. Using such mechanisms, diagnostic information concerning the patient is entered by the physician and the "wizard" suggests device parameters to be programmed.

BRIEF SUMMARY OF THE INVENTION

The present invention provides an improved programming wizard particularly optimized to simplify implantation of subcutaneous heart rhythm and/or hemodynamic monitors responsive to pressure, Oxygen saturation, activity, or the like. In the specific context of programming of subcutaneous electrograms monitors, the wizard provides an increased level of simplicity with regard to the set-up of criteria for arrhythmia detection and for prioritizing storage of electrograms associated with detected arrhythmias.

The invention is particularly beneficial in the context of devices implanted using minimally invasive techniques, for example as performed in a physician's office on an outpatient basis. Methods of minimally invasive implantation are set forth in U.S. Pat. Nos. 6,412,490, 6,496,715, US Patent Publication Nos. 20090036917, 20100094252 and 20100283705, all incorporated herein by reference in their entireties.

In one embodiment of the invention, the patient's age is used to automatically set arrhythmia detection parameters, for example by controlling rate-based criteria associated with tachycardia detection.

In another embodiment of the invention, the primary reason for monitoring using the implanted device is employed to prioritize waveform storage. Primary reasons may include, for example, syncope, palpitations, seizures, ventricular tachycardia, suspected AF, AF ablation, AF management, cryptogenic stroke or other unspecified reason. In addition to or as an alternative to use of the prioritization scheme to control storage of monitored waveforms, the device may employ the prioritization mechanism to prioritize regular transmissions of stored data in order to conserve battery life.

These embodiments offer the opportunity to shorten and simplify the implant ant set-up of the implantable devices, prolong battery life and optimize use of limited memory storage capabilities.

DETAILED DESCRIPTION OF THE PREFERRED EMBODIMENTS

Figure 1:
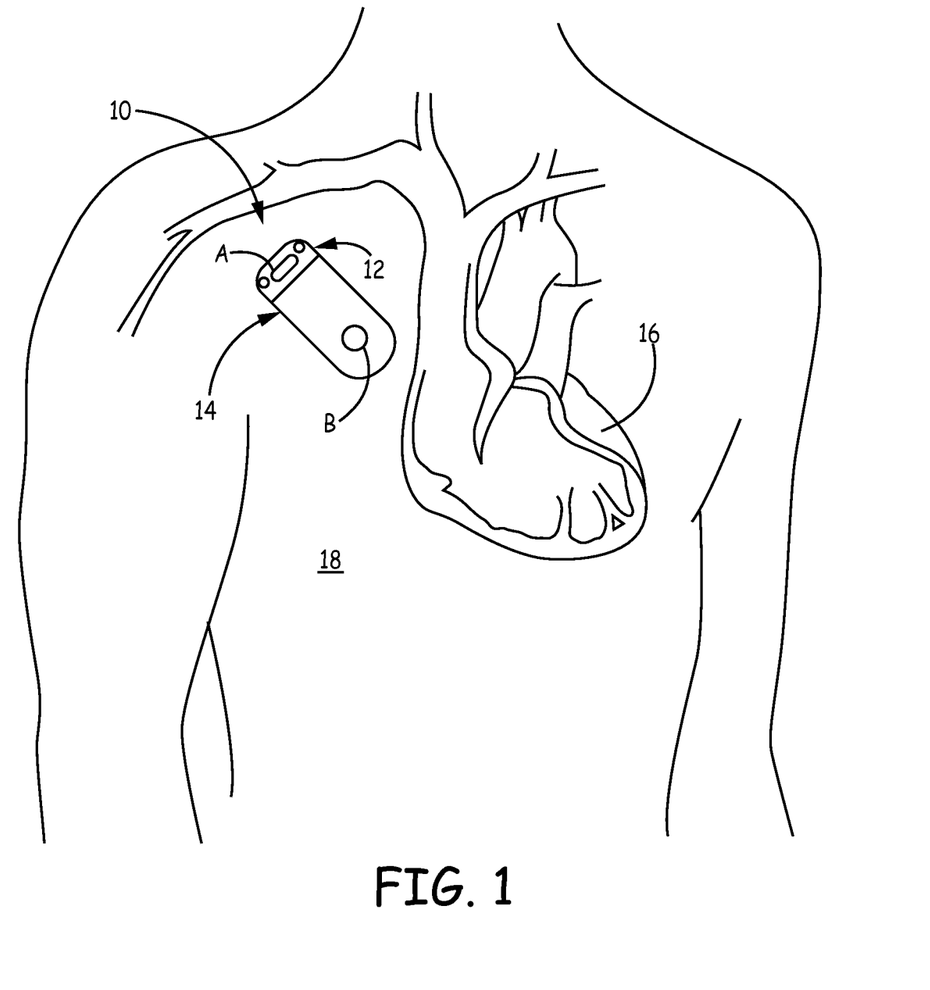
FIG. 1 is a diagram illustrating an IMD of the sort to which the invention applies, implanted in a patient.

FIG. 1 is a simplified schematic view of an implantable cardiac monitor 10 benefitting from the improvements of the present invention implanted subcutaneously in the upper thoracic region of the patient's body 18 and displaced from the patient's heart 16. The housing of the cardiac monitor 10 (shown enlarged in scale to the body 18) and comprises a non-conductive header module 12 attached to a hermetically sealed enclosure 14. The enclosure 14 contains the operating system of the cardiac monitor 10 and is preferably conductive but may covered in part by an electrically insulating coating. A first, subcutaneous, sense electrode A is formed on the surface of the header module 12 and a second, subcutaneous, sense electrode B is formed by an exposed portion of the enclosure 14. A feedthrough extends through the mating surfaces of the header module 12 and the enclosure 14 to electrically connect the first sense electrode A with the sensing circuitry within the enclosure 14, and the conductive housing electrode B is directly connected with the sensing circuitry. One form of coupling the header module 12 and enclosure 14 together is disclosed in commonly assigned U.S. Pat. No. 5,851,221, incorporated herein by reference.

The electrical signals attendant to the depolarization and re-polarization of the heart 16 are referred to as the cardiac EGM and are sensed across the sense electrodes A and B. The cardiac monitor 10 is sutured to subcutaneous tissue at a desired orientation of its electrodes A and B to the axis of the heart 16 to detect and record the EGM in a sensing vector A-B for subsequent uplink telemetry transmission to an external programmer (shown in FIG. 2).

In general, the hermetically sealed enclosure 14 includes a lithium battery, circuitry that controls device operations and records arrhythmic EGM episode data in memory registers, and a telemetry transceiver antenna and circuit that receives downlink telemetry commands from and transmits stored data in a telemetry uplink to the external programmer. The circuitry and memory may be implemented in discrete logic or a micro-computer based system with A/D conversion of sampled EGM amplitude values. One exemplary operating system that can be modified in accordance with the present invention is described in the above-incorporated '209 PCT application.

Figure 2:
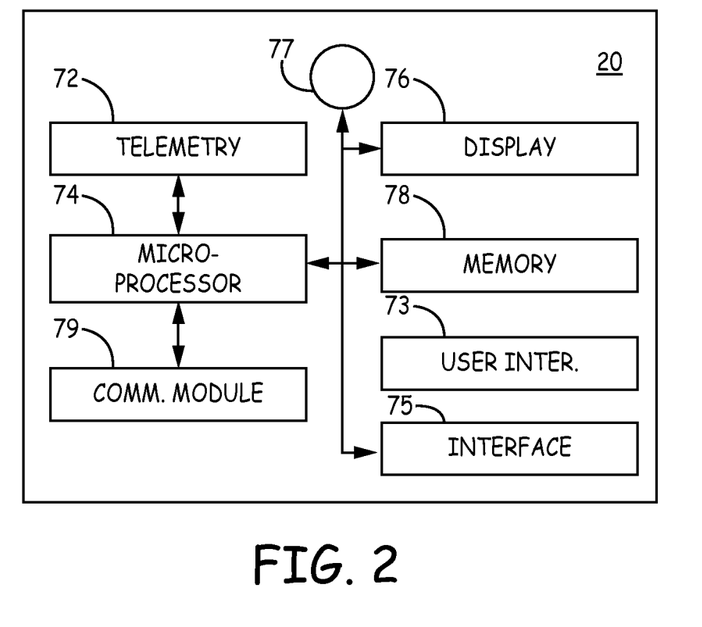
FIG. 2 is a functional block diagram of typical components included in a typical external programmer of the sort in which the invention may usefully be practiced.

FIG. 2 is a functional block diagram of typical components included in an external programmer. In one method for practicing the present invention, programmer 20 is located in a clinic or other medical facility and used for interrogating and programming IMDs for multiple patients. Automatic control of telemetry link status between programmer 20 and an IMD reduces the likelihood of inadvertent programming or interrogation of the IMD. Aspects of the present invention for automatically controlling the status of a telemetry link may be incorporated in any system used for communicating with an IMD such as systems including a home monitor, patient programmer, or other external device enabled for programming or interrogating an IMD. The use of the term "programmer" herein is therefore not intended to be limiting to a particular type of external device but refers generally to any external device enabled to establish a communication link with an IMD and with which automatic control of telemetry link status is desired.

Programmer 20 shown in FIG. 2 includes a telemetry circuit 72 for bidirectional communication with an IMD, such as IMD 10 shown in FIG. 1. Programmer 20 may be a microprocessor-controlled device wherein microprocessor 74 operates with associated memory 78 for controlling programmer functions, including automatic telemetry link status control in accordance with the present invention.

Memory 78 is used alone or in combination with IMD memory 56 (FIG. 1) to store information used in telemetry link control operations. Such information may include conditions for verifying a telemetry session is active or inactive, time intervals for monitoring for such conditions, and messages that may be displayed during a telemetry termination operation. Parameters used in controlling telemetry link status may be fixed values stored in memory 78 (and/or IMD memory) or customized values programmable by a clinician using user interface 73.

In order for the clinician to interact with programmer 20, a keyboard, graphical user interface, or other user interface 73, coupled to microprocessor 74, is provided. Display 76 and/or the user interface 73 allow a user to enter command signals to initiate transmissions of downlink or uplink telemetry and to initiate and control telemetry sessions once a telemetry link with an implanted device has been established. Other types of user interaction mechanisms and electronics may be implemented such as voice recognition/response systems.

Display 24 is used to display patient related data, menu choices and data entry fields used for entering data during a telemetry session. Display screen 24 also displays a variety of screens of retrieved IMD data, previously stored or in real time and may display uplinked event signals as they are received and thereby serve as a means for enabling the user to timely review IMD operating history and status. Display 76 is used for displaying messages to a user regarding telemetry link status during the telemetry link control operations provided by the present invention. A speaker 77 may also be provided for broadcasting audible tones or messages used to alert the user to telemetry, programming, and/or interrogation status or conditions.

Programmer 20 may include a communications module 79, which may be embodied as a modem, used for transferring data to a central database or communicating with other patient management systems. Programmer 20 may further include an interface 75 for coupling peripheral devices which may include external monitoring equipment such as ECG leads, blood pressure monitor, etc.

Exemplary programmers in which the invention may be practiced include those described in U.S. Pat. Nos. 4,550, 370, 6,230,059, 7,528,094 and 6,381,493, all incorporated herein by reference in their entireties.

Figure 3:
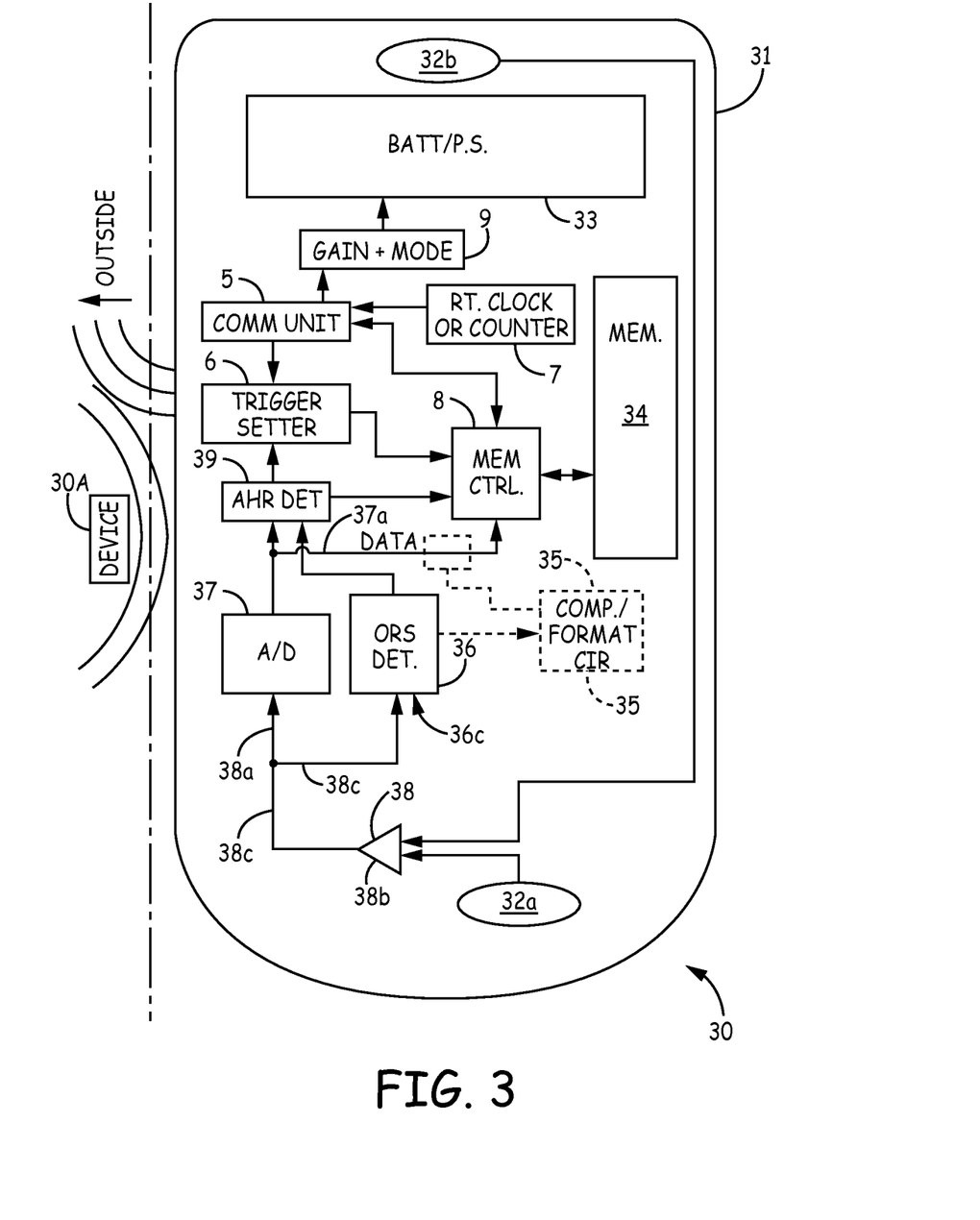
FIG. 3 is a block diagram of typical functional components of an IMD of the sort to which the invention applies.

FIG. 3 illustrates an exemplary circuit 30 for an IMD which may benefit from the present invention. Circuit 30 is illustrated in an outline of an implantable device shell 31. Electrodes 32a and 32b bring signal from the body to an input mechanism 38, here drawn as a differential amplifier for simplicity only, the output of which is fed to a QRS detector 36 and an A/D converter 37.

Both these circuits 36 and 37 supply output to an arrhythmia detector 39, which in this preferred embodiment supplies the autotrigger signal to the trigger setting circuit 6. The data output from the analog to Digital converter may be converted, compressed, formatted and marked or reformulated if desired in a circuit 35 before the data is ready for input into the memory 34. The Memory control circuits 8 receives input from the A/D converter, with or without conversion and so forth from circuit 35, from the auto triggering determination circuit (here seen as the arrhythmia detection circuit) 39 (which may include input directly from the QRS detector if desired) as well as signals from the trigger setter circuit 6. The trigger setter circuit may also be controlled by a communications unit 5 which operates to receive and decode signals from the outside of the implant 30 that are telemetered or otherwise communicated in by a user.

This communications unit 5 will also be able to communicate with the memory controller to request the offloading of memory data for analysis by an outside device. It should contain an antenna and/or other transceiver device or circuitry to communicate with an outside device such as device 30A, which may correspond to the programmer of FIG. 2. A clock or counter circuit 7 reports the time since start or real time to the outside interrogator device 30A contemporaneously with a data offloading session so that the events recorded in memory 34 may be temporally pinpointed.

Known alternatives to this overall design, for example as disclosed in the above-cited references may also be employed. For example, a microprocessor may be employed to accomplish some or all of the functions of circuits 6, 8, 39, and 35.

The implantable device preferably has the capability to detect a variety of arrhythmias. An exemplary arrhythmia detection methodology is set forth below. Arrhythmia detection methodologies taken from the references cited above may be substituted.

The device, for example, may be capable of detecting a pause (Asystole), bradycardia, ventricular tachyarrhythmias, and atrial tachyarrhythmias. Pause, bradycardia, and ventricular tachyarrhythmia detection algorithms may act on a beat-by-beat basis. An automatic episode is declared when episode detection criteria are met.

Atrial tachyarrhythmias may be detected on the basis of evidence accumulated in 2-minute segments. Time intervals between events, i.e., R-R intervals, may be used to build evidence for an atrial arrhythmia Pauses can be related to syncope which is one of the main reasons for implanting the device. A Pause episode (Asystole) may be detected when the interval from the previous sensed event to the current event (ventricular sense, escape time-out, or an over ranged ECG signal) exceeds the programmed Pause Duration. Pause episodes may be rejected by the device when the device detects evidence of low signal amplitude at the time of detection. A pause episode may terminate after twelve sensed events.

Bradycardia may also be detected. Bradycardia is clinically defined as a resting heart rate less than 60 bpm. It sometimes results in fainting and dyspnea. When an R-R interval is longer than the programmed Brady Detection Rate, the associated event may be counted as a Brady event. When the number of consecutive Brady events exceeds the programmed Brady Number of Intervals to Detect, a Brady episode may be detected. The Brady episode may terminate after four consecutive R-R intervals shorter than Brady Detection Rate occur.

Documented episodes of Ventricular Tachycardia increase the risk of SCD. The device is capable of detecting episodes of Tachycardia. A goal may be to detect episodes of ventricular tachycardia. Detection is typically based on the ventricular cycle length and duration. The device may have two detection zones within the tachycardia detection algorithm. One zone is designed for detecting ventricular tachycardia (VT) and is based on a consecutive counter scheme. The other zone is designed for detecting fast ventricular tachycardia (FVT) and is based on a probabilistic counter scheme. The VT zone may be programmable by the user. The FVT may be fixed and not programmable by the user.

Events falling into either zone may count towards Tachy Detection, however each zone is unique in how it detects tachycardia. The CTDI (Consectitive Tachycardia Detection Interval) may be a consecutive counter zone that allows programming of both the ventricular cycle length (CTDI) and duration (Consecutive Number of Beats to Detect (CNID)). When Tachy Detection is enabled, an R-R interval shorter than the programmed CTDI is counted as a Tachy event. The count of Tachy events is reset to 0 if an R-R interval occurs that is greater than or equal to the CTDI. A Tachy episode may terminate after eight consecutive sensed events are greater than or equal to the CTDI or 20 seconds elapse with the RR Median greater than the CTDI. The PTDI (Probabalistic Tachycardia Detection Interval) maybe a probabilistic counter zone that has a fixed PTDI and a fixed duration (Probabilistic Number of Intervals to Detect—PNID). PNID is a combination of two numbers; number of events and a window of events.

In a preferred embodiment of the invention, programming of the CTD! Is simplified by automatically selecting a corresponding detection rate equal as a function of the patient's age. For example, The CTDI may correspond to 230 bpm minus the patient's age. In other embodiments, other detection criteria as discussed herein may be set based upon the patient's age may similarly automatically programmed in an analogous manner.

When Tachy Detection is enabled, an R-R interval shorter than the programmed PTDI the event is counted as a Tachy event. If the number of Tachy events reaches the Probabilistic Threshold, the first number in the programmed PNID, a Tachy episode is detected. The count of the number of recent Tachy events is limited to the Probabilistic Detection Window, the second number in the programmed PNID. The threshold may be 75% of the Probabilistic Detection window.

Combined Count Detection may be automatically enabled when Tachy Detection is enabled. If the number of Probabilistic events is 6 or more, Combined Count detection occurs if the sum of the Tachy events reaches the Combined Number of Intervals to Detect (CNID). CNID may be equal to INT [(7* Probabilistic Threshold)/6]. The device is capable of detecting both atrial fibrillation and atrial tachycardia.

The device preferably detects atrial fibrillation (AF) despite the fact that P-waves are not detected. Instead of using atrial rate and A-V pattern information the patterns of variability of R-R intervals may be analyzed using the Cluster Signature Metric to make a determination of whether the patient is in atrial fibrillation.

The Cluster Signature Metric (CSM) analyzes changes in R-R intervals to help infer patterns in the ventricular conduction in a Lorenz plot. Since AT and AF have unique signatures of ventricular conduction, this information cannot only detect the presence of an atrial arrhythmia; it can also help distinguish between AT and AF. Since no atrial information is available in the device, to increase the power of the detector, these R-R interval patterns are analyzed over an extended (two minute) period of time. The algorithm uses this information to report the AT or AF status on every two minute interval.

The AF Detection algorithm may use evidence of premature atrial contractions (PACs) and premature ventricular contractions (PVCs) to help increase specificity by avoiding detection due to prolonged ectopy. AF detection is independent of ventricular detection. An AF episode can be detected at the same time as one of these episodes. Atrial episode termination may be independent of concurrent ventricular episodes. Termination of an AF episode occurs on the 2-minute interval.

Atrial Tachycardia (AT) may be detected based on the pattern of RR variability exhibited in 2-minute periods, using one of two algorithms: one that looks for very regular RR intervals (Regularity Evidence), or another that uses Regularity Evidence (to account for variations due to autonomic modulation of the AV node) and the Lorenz plot to look for regularly irregular RR intervals (variations due to autonomic modulation of AV node and changes in conduction ratio), or irregular RR intervals (variations due to modulation of AV node refractoriness by irregular atrial activation, autonomic modulation of AV node and changes in conduction ratio).

While in embodiments intended for relatively short term use, (e.g. 2 or 3 years) it is envisioned that the implanted device will not need to update the arrhythmia detection parameters. However, in longer lived devices, for example in the case of rechargeable devices, the processor within the implanted device may include programming commands configured to regularly (e.g. yearly) update the patient's age based upon the processors real-time clock capabilities in a conventional fashion. In such embodiments, the fact that the patient ages can be used to provide automatic updating of the detection criteria in a simple manner.

When an arrhythmia is detected, detailed ECG and episode summary information is stored for later review by the physician. An exemplary automatic episode storage methodology is set forth below.

In a preferred embodiment, An AF or AT episode can occur simultaneously with one of the other types of episodes (asystole, Brady, or Tachy). If this occurs, the system stores episode-related information and an ECG strip for each episode independently. No other combinations of automatic episodes can occur simultaneously.

A limit will be set on the number of automatic episodes stored per day (midnight-midnight). This is to prevent premature battery depletion. Once the device has collected a fixed number of episodes in a day (e.g. 27) the following scheme will apply: episodes will only be detected and stored for episode types for which the minimum number of episodes to be collected has not been met. For AF episodes, the device will continue to detect and store the longest AF episode.

In one embodiment, for each automatically stored episode type other than AF or AT, 30 seconds of ECG data, R-R intervals, Marker Channel annotations, and annotations for detection criteria is stored prior to detection, and up to 27 seconds is stored prior to episode termination. If the duration of the episode from detection to termination is less than 27 seconds, then less than 27 seconds prior to episode termination is stored.

In order to simplify programming of episode storage, the present invention may provide automatic selection of AF waveform storage prioritization. For Example for each AF or AT episode, two minutes of ECG data, R-R intervals, and Marker Channel annotations will be stored prior to detection. No data will be stored at the time of episode termination. If AF Detection is enabled, then storage of ECG for AF episodes can be made conditional with respect to the duration of the detected episode by programming a duration threshold. If the detected episode duration is shorter than this threshold then ECG is not stored and episode log information is not stored.

The selection of AF episode storage priority may be coupled to a physician entered indication of the primary reason for monitoring the patient as discussed above. For Example, for the following list of reasons for monitoring, the following rules for AF storage may automatically be programmed;
  a) syncope—Longest AF episode only;
  b) palpitations—AF episodes greater or equal to 6 minutes;
  c) siezures—AF episodes greater or equal to 10 minutes;
  d) ventricular tachycardia—AF episodes greater or equal to 10 minutes;
  e) suspected AF—AF episodes greater or equal to 6 minutes;
  f) AF ablation—All
  g) AF management—All
  h) cryptogenic stroke—All
  i) other unspecified reason—AF episodes greater or equal to 10 minutes.

In other embodiments of the invention, the reasons for monitoring or other diagnostic classifications might also be employed to prioritize which episodes of ventricular arrhythmias might be stored in an analogous fashion.

When a new episode is detected, its associated ECG strip will always be stored. However, if the memory is already full due to previously detected episodes, an older ECG strip will be overwritten. The ECG strip that will be overwritten will be the oldest strip for an episode type of Pause, Brady, Tachy, or AT that has more than three episodes stored or for an episode type of AF that has four episodes stored. In this way, the system will have at least three episodes of Pause, Brady, Tachy, AT, and at least four episodes of AF available for review at follow-up, with preference given to the most recently detected episodes.

As noted above, the prioritization mechanism of the present invention may also be employed to prioritize data for transmission to an external device. For example, the device may be configured to transmit a selected set of information and stored waveforms on a daily basis. Even if the device memory is capable of holding more stored information for in-office downloading, the prioritization mechanism discussed above may be used in an analogous fashion to select a subset of the stored data for transmissions which occur on a more frequent basis.

In such an embodiment the reason for implantation, as entered into the programmer, may be used by the implanted device define a prioritized set of waveforms for long term storage as well as a prioritized reduced set of waveforms for daily transmission.

Figure 4:
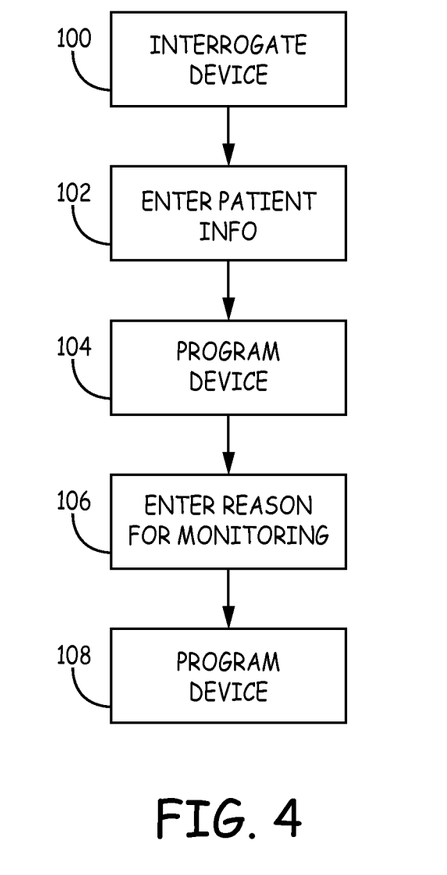
FIG. 4 is a flow-chart generally illustrating the operation of the invention.

FIG. 4 is a simplified flow chart illustrating the automatic programming functions provided by one embodiment of the present invention. At 100, the programmer interrogates the device to initiate communication. At 102, the Physician enters patient related information into the programmer. This information may include the patient's age, as discussed above. At 104, the programmer programs the device, including arrhythmia detection parameters. As discussed above, at this step, the programmer may select a tachycardia detection rate or interval based upon the patient's age. In some embodiments, other detection parameters might also be automatically programmed based upon patient age.

At 106 the physician enters the reason for monitoring into the programmer. At 108, the programmer programs the types of detected atrial fibrillation episodes that will be stored by the implanted device for later retrieval and/or transmission. As discussed above, other types of storage prioritization and/or transmission may also be automatically programmed in an analogous fashion.

In conjunction with the above disclosure, we claim:
1. A method of programming an implantable cardiac monitoring device, comprising:
  in a programmer, detecting entry of a patient's age;
  thereafter transmitting programming commands from the programmer to the implantable cardiac monitoring device including an arrhythmia criterion selected as a function of the patient's age;
  in the programmer, detecting entry of a reason for monitoring;
  thereafter transmitting programming commands from the programmer to the implantable cardiac monitoring device including a prioritization of an arrhythmia storage criterion, the cardiac monitoring device having first and second sense electrodes on a housing of the device, wherein the implantable cardiac monitoring device is a leadless implantable cardiac device; and
  responsive to receipt of the programming commands, employing the implantable device to detect the arrhythmia according to the criterion and employing the implantable cardiac device to store records of the arrhythmia according to the prioritization.

2. A method according to claim 1 wherein the arrhythmia comprises a ventricular tachyarrhythmia.

3. A method according to claim 1 wherein the criterion is a rate or interval based criterion.

4. A method according to claim 3, wherein the criterion is set based upon a subtraction of the patient's age from a preset rate.

5. A system comprising:
a programmable implantable cardiac monitoring device having first and second sense electrodes on a housing of the device, a programmer, responsive to entry of a patient's age, the programmer configured to thereafter transmit a programming commands from the programmer to the implantable device including an arrhythmia detection criterion and responsive to entry of a reason for monitoring, the programmer configured to thereafter transmit programming commands from the programmer to the implantable device including a prioritization of an arrhythmia storage criterion; and
wherein the implantable device is configured to, responsive to receipt of the programming commands, thereafter detect the arrhythmia according to the criterion and transmit records of the arrhythmia according to the prioritization, wherein the implantable cardiac monitoring device is a leadless implantable cardiac monitoring device.

6. A system according to claim 5 wherein the reason for monitoring includes one of syncope, palpitations, seizures, ventricular tachycardia, suspected AF, AF ablation, AF management or cryptogenic stroke.

7. A system according to claim 5 wherein the arrhythmia comprises atrial fibrillation.

8. A system according to claim 5 wherein the prioritization is based upon duration of the arrhythmia.

9. A system comprising:
a programmable implantable cardiac monitoring device having first and second sense electrodes on a housing of the device, a programmer, responsive to entry of a patient's age, the programmer configured to thereafter transmit a programming commands from the programmer to the implantable device including an arrhythmia detection criterion and responsive to entry of a reason for monitoring, the programmer configured to thereafter transmit programming commands from the programmer to the implantable device including a prioritization of an arrhythmia storage criterion; and
wherein the implantable device is configured to, responsive to receipt of the programming commands, thereafter detect the arrhythmia according to the criterion and store records of the arrhythmia according to the prioritization, wherein implantable cardiac monitoring device is a leadless implantable cardiac monitoring device.

10. A system according to claim 9 wherein the arrhythmia comprises a ventricular tachyarrhythmia.

11. A system according to claim 9 wherein the criterion is a rate or interval based criterion.

12. A system according to claim 11, wherein the criterion is set based upon a subtraction of the patient's age from a preset rate.

13. A system according to claim 12, wherein the implantable device is configured to, responsive to passage of time, update the patient's age and the detection criterion thereafter detect the arrhythmia according to the updated criterion.

14. A method according to claim 1 wherein the reason for monitoring includes one of syncope, palpitations, seizures, ventricular tachycardia, suspected AF, AF ablation, AF management or cryptogenic stroke.

15. A method according to claim 1 wherein the arrhythmia comprises atrial fibrillation.

16. A method according to claim 1 wherein the prioritization is based upon duration of the arrhythmia.

17. A system according to claim 9 wherein the reason for monitoring includes one of syncope, palpitations, seizures, ventricular tachycardia, suspected AF, AF ablation, AF management or cryptogenic stroke.

18. A system according to claim 9 wherein the arrhythmia comprises atrial fibrillation.

19. A system according to claim 9 wherein the prioritization is based upon duration of the arrhythmia.

* * * * *